United States Patent
Bradway et al.

(10) Patent No.: US 11,497,632 B2
(45) Date of Patent: Nov. 15, 2022

(54) SPRING BARB FOR MEDICAL DEVICE

(71) Applicant: Cook Medical Technologies LLC, Bloomington, IN (US)

(72) Inventors: Ryan Bradway, West Lafayette, IN (US); Charles Baxter, West Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 81 days.

(21) Appl. No.: 16/524,999

(22) Filed: Jul. 29, 2019

(65) Prior Publication Data

US 2020/0030123 A1    Jan. 30, 2020

Related U.S. Application Data

(60) Provisional application No. 62/711,900, filed on Jul. 30, 2018.

(51) Int. Cl.
*A61F 2/848* (2013.01)
*A61F 2/01* (2006.01)
*A61F 2/07* (2013.01)

(52) U.S. Cl.
CPC .............. *A61F 2/848* (2013.01); *A61F 2/01* (2013.01); *A61F 2/07* (2013.01); *A61F 2002/8483* (2013.01); *A61F 2220/0016* (2013.01); *A61F 2220/0058* (2013.01)

(58) Field of Classification Search
CPC .... A61F 2/848; A61F 2/07; A61F 2/86; A61F 2002/8483; A61F 2002/823; A61F 2220/0008; A61F 2220/0016; A61F 2/01; A61F 2220/0058; F41H 11/08; E04H 17/04; E04H 17/045; A61B 17/12172; A61B 2017/00579

See application file for complete search history.

(56) References Cited

U.S. PATENT DOCUMENTS

| 6,520,974 | B2 | 2/2003 | Tanner et al. | |
| 6,802,858 | B2 * | 10/2004 | Gambale | A61F 2/06 623/1.15 |
| 7,081,132 | B2 | 7/2006 | Cook et al. | |

(Continued)

FOREIGN PATENT DOCUMENTS

| EP | 2331027 | 6/2011 |
| WO | WO2010/024881 | 3/2010 |

OTHER PUBLICATIONS

Childs, Peter RN. "Interference Fits." Mechanical Design Engineering Handbook, Butterworth-Heinemann, 2014, pp. 767-769. (Year: 2014).*

(Continued)

*Primary Examiner* — Yashita Sharma
(74) *Attorney, Agent, or Firm* — Crowell & Moring LLP

(57) ABSTRACT

Disclosed herein is an anchor for use with a medical device. The anchor includes a coil, a barb, and a turn connecting the coil to the barb. The anchor may be made of a shape memory material. The coil may have a first handedness, and the turn may have a second handedness opposite the first handedness. The anchor may be attached to the medical device by a friction fit, in some cases without being attached by welding, soldering, adhesive, or crimping.

20 Claims, 5 Drawing Sheets

(56) References Cited

U.S. PATENT DOCUMENTS

| | | | |
|---|---|---|---|
| 7,828,839 B2* | 11/2010 | Cook | A61F 2/848 623/1.36 |
| 7,905,915 B2 | 3/2011 | Young et al. | |
| 8,029,559 B2 | 10/2011 | Sisken et al. | |
| 8,348,988 B2 | 1/2013 | Lad et al. | |
| 8,696,739 B2* | 4/2014 | Dierking | A61F 2/848 623/1.36 |
| 8,747,457 B2* | 6/2014 | Petersen | A61F 2/07 623/1.36 |
| 9,192,463 B2* | 11/2015 | Paul, Jr. | A61F 2/06 |
| 9,237,959 B2 | 1/2016 | Cage | |
| 9,642,734 B2 | 5/2017 | Melanson et al. | |
| 2005/0159804 A1 | 7/2005 | Lad et al. | |
| 2008/0033534 A1 | 2/2008 | Cook et al. | |
| 2009/0171442 A1 | 7/2009 | Young et al. | |
| 2012/0022638 A1 | 1/2012 | Leewood et al. | |
| 2016/0256257 A1 | 9/2016 | Rasmussen et al. | |

OTHER PUBLICATIONS

Extended European Search Report for 19189220.7 dated Nov. 21, 2019, 5 pgs.

Office Action In Corresponding European Application No. 19189220.7, dated Dec. 8, 2020 (5 pages).

\* cited by examiner

SPRING BARB FOR MEDICAL DEVICE

BACKGROUND

The present application generally relates to medical devices. More particularly, the present application relates to an anchor for an intravascular implant, and the implantable device itself.

Medical devices that are permanently or temporarily deployed to the lumen of a body vessel are generally placed with precision, into areas of the body that require treatment. These devices generally perform ideally when they remain at the site to which they were deployed. In order to retain these devices in such locations, a number of fixation methods have been developed. These methods vary depending on the function, size, and location to be deployed for each device, and include the use of adhesives, sizing techniques, and mechanical attachments, among others.

One type of mechanical attachment that has been used with frequency in the field of medical devices is the barb. A number of considerations are generally taken into account when employing a barb in a body lumen: the strength required to support the device, the degree to which the barb is to permitted to pierce a vessel wall, and the means by which the barb is to be incorporated onto the body, among others.

A particular type of medical implant that has been used with barbs to anchor the device in place is the stent. In some instances, stents are made of shape memory materials. Wire stents made of shape memory materials can provide improved fatigue properties and delivery system profiles compared to, for example, stainless steel stents. These advantages may be more pronounced in, for example, a seal or fixation stent of a stent graft, where relatively larger radial force is desired. However, attaching barbs to shape memory material stents, including those made of shape memory alloys such as nickel-titanium alloys, can be difficult. Soldering a barb onto the nickel-titanium device has the potential to affect the fatigue properties of the alloy, and there may be degradation of the solder joint over time. Integrated barbs in a cannula cut stent are presently employed, but cannula-cut barbed stents are generally more expensive than those made of wire. Therefore, a solution in which an anchor including a barb which is made of wire, for attachment to a device component which is likewise made of wire, may be economically desirable.

It has been a challenge to develop a barb for use with a wire, shape memory material medical device.

SUMMARY

In one aspect, the present disclosure provides a medical device for implantation into a body vessel. The medical device may include at least one elongate member. The medical device may include an anchor disposed about the elongate member. The anchor may have a first end and a second end and include a coil defining a longitudinal axis therethrough. At least a portion of the coil may surround the elongate member. The anchor may include a barb including the second end. The anchor may have a turn of at least 90 degrees and a bend, the turn and the bend connecting the coil to the barb, such that the barb and the longitudinal axis of the coil define an acute angle therebetween.

In another aspect, the present disclosure provides a medical device for implantation into a body vessel. The medical device may include at least one elongate member. The medical device may include an anchor disposed about the elongate member. The anchor may have a first end and a second end and include a coil having a first handedness and an inner diameter in a free condition about 70% to about 95% a diameter of the elongate member at the point of attachment. The anchor may have a barb including the second end, and a turn connecting the coil to the barb, such that the second end is disposed proximate the first end. The turn may a second handedness opposite the first handedness. The anchor may be fixed to the elongate member by a friction fit. The anchor may be fixed to the elongate member by means other than a crimp, a weld, a solder joint, and an adhesive.

In another aspect, the present disclosure provides an anchor having a first end and a second end and including a coil, a barb including the second end, and a turn connecting the coil to the barb, such that the second end is disposed proximate the first end. The second end may define a point, such that the barb may be a barb.

Further objects, features and advantages of this system will become readily apparent to persons skilled in the art after a review of the following description, with reference to the drawings and claims that are appended to and form a part of this specification.

DETAILED DESCRIPTION

The drawings are purely schematic illustrations of various aspects of the invention and are not necessarily to scale, unless expressly stated.

The terms "substantially" or "about" used herein with reference to a quantity includes variations in the recited quantity that are equivalent to the quantity recited, such as an amount that is equivalent to the quantity recited for an intended purpose or function. "Substantially" or derivatives thereof will be understood to mean significantly or in large part. When used in the context of a numerical value or range set forth, "about" or "substantially" means a variation of ±15%, or less, of the numerical value. For example, a value differing by ±15%, ±14%, ±10%, or ±5%, among others, would satisfy the definition of "about."

Figure 1:
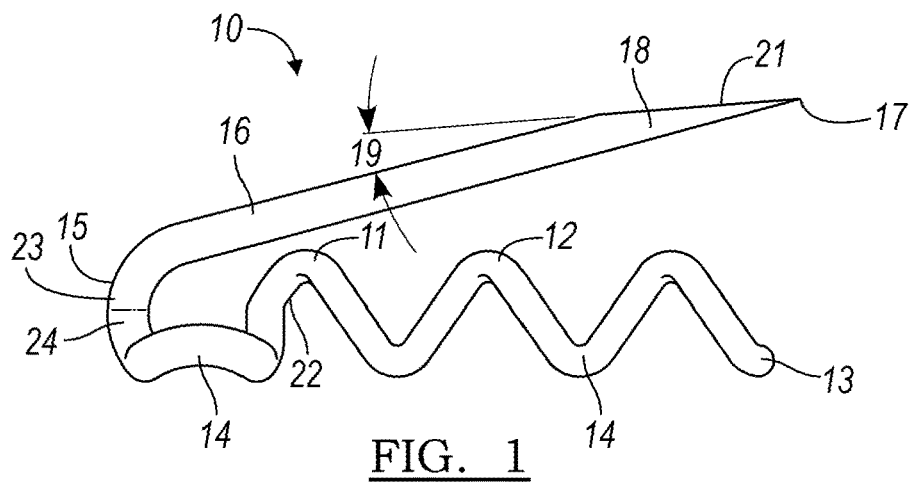
FIG. 1 is a side view of an anchor constructed in accordance with the principles of the present invention.

In a first aspect, an anchor 10 for a medical device is illustrated in FIG. 1. The anchor 10 is integrally constructed of a single segment of wire, and includes a coil 12, a turn 14 leading into a bend 15, and a barb 16. The coil 12 may be a coarse pitch coil. The turn 14 joins the coil 12 to the barb 16, and is formed from a portion along the length of the wire used to make the anchor 10 which lies between the first end 13 and the second end 17.

The barb 16 may be sharpened, yielding a pointed end 18. However, in some embodiments, the barb 16 may be made of a thin enough wire to act as the barb without further sharpening. The barb 16 is a structure that is capable of engaging the wall of a body passage and anchoring the device therein. The barb 16 may be a substantially straight section of wire, or may be have a gentle bend or slight angle, so long as the anchor 10 is still capable of holding a the medical device within the body passage.

If sharpened, the point of pointed end 18 may be formed, such as by a cut, such that it has a smooth and continuous termination. This design serves to tighten the hold on the tissue into which the pointed end 18 is to be inserted. In the embodiment shown in FIG. 1, the angle 19 formed between the barb 16 and the face 21 generated by the cut is about 10 degrees, but may be from about 2.5 degrees to about 30 degrees, or from about 5 degrees to about 20 degrees, or from about 7.5 degrees to about 15 degrees.

Because of the turn 14, the pointed end 18 points back toward first end 13. This results in the second end 17 being proximate the first end 13. In some instances, the second end 17 may be closer to the first end 13 than it is to the apex 24, which, in the illustrated embodiment, is positioned at the transition point 22 loop 14 and bend 15 of the anchor 10. This construction can result in lengthening and tightening of the coil 12 around the structure about which the coil 12 is disposed, such as a wire strut of a medical device. When used as an anchoring portion of a medical device, hemodynamic forces cause tightening of the grip of the anchor 10 on the strut to which the anchor is attached. That is, when force pushes in a direction that would otherwise dislodge the device from the tissue, the coil 12 reacts by stretching and as a result tightening around the structure on which it is disposed. The turn 14 and bend 15 also allow for ease in manufacture of the anchor 10, and permit it to be made unitarily, from a single piece of precursor wire, such as a shape memory wire. The bend 15 also causes the barb 16 of the anchor 10 to lie tangent a strut to which the anchor 10 is fixed.

In one embodiment, the coil 12 has a first helical handedness and the turn has a second helical handedness which is opposite the first helical handedness. The handedness of a helix may be determined by viewing the helix, or coil, down the helical axis around which it winds. In the case of the present disclosure, the handedness of the coil is defined by the direction in which the coil winds when viewed down the helical axis with the first end 13 closest the viewer. If the coil extends clockwise, it is a right-handed helix; if it extends counterclockwise, its handedness is instead left-handed.

In an anchor 10 having a right-handed coil 12, the turn 14 would reverse and be a left-handed turn. In an anchor 10 having a left-handed coil 12, the turn 14 would instead be a right-handed turn. The change in rotational direction between the coil windings 11 and the turn 14 provides an effective location for a point of resistance to force directed in such a way that would otherwise compress the coil 12, thereby defining a second end to the coil 12 at the position where the turn 14 begins. The coil 12 has a coil length between the first end 13 of the anchor and the transition point at the interface of the coil 12 and the turn 14. The turn 14 may proceed for at least about 90 degrees rotationally, in some embodiments representing a turn of about 135 degrees, or about 180 degrees, or about 225 degrees, or about 270 degrees, or about 315 degrees, or about 360 degrees.

The measurements of portions of the anchor 10 will vary based on its usage. In one example, the length of the barb 16, from the second end 17 to the end of the bend 15 at transition point 23, may be about 5 millimeters (mm). The uncompressed length of the coil 12 between first end 133 and transition point 22 may be about 4 mm in this anchor 10, with a helical pitch (that is, the linear distance between corresponding portions of consecutive windings 11) of 1.5 mm. The barb 16 may be angled at about 15 degrees relative to the helical axis of coil 12. Such an anchor 10 may be made of a shape memory alloy, such as a nickel-titanium alloy, which is a wire, the wire having a diameter of about 0.012 inch (0.3048 mm.) In one embodiment, the coil 12 may have a length which is at least double its pitch, but this value may be varied as long as a friction fit between the anchor and the medical device body may be maintained.

Instead of a shape memory alloy, the anchor of the present disclosure may be made of or include stainless steel, or titanium. The anchor may be made of another biocompatible metal and have a coating to inhibit corrosion thereof.

Figure 2:
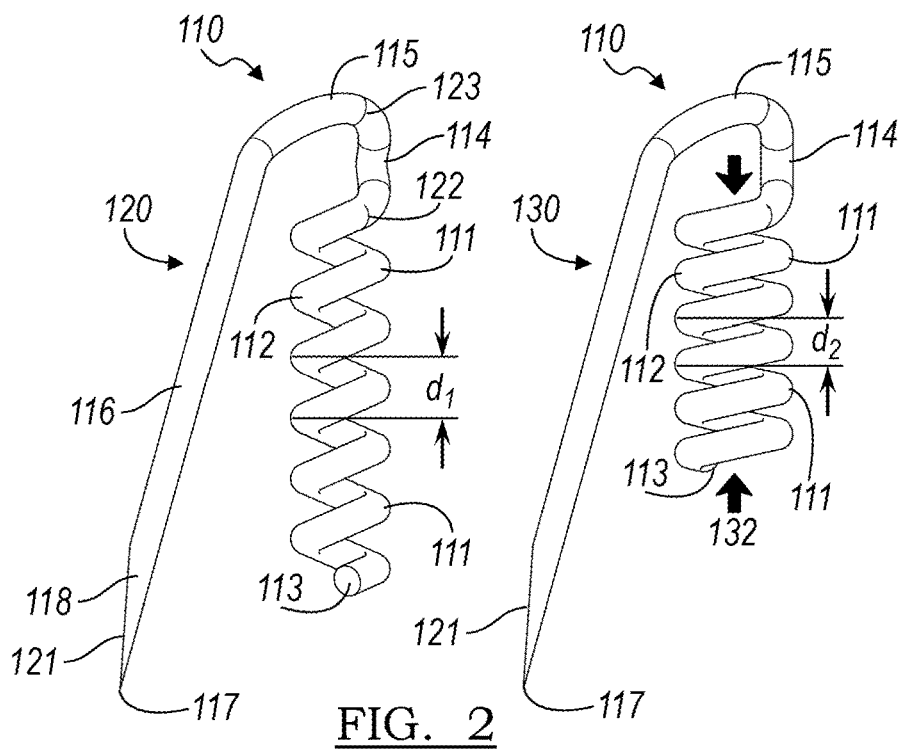
FIG. 2 is views of another anchor constructed in accordance with the principles of the present disclosure in an expanded and in a compressed condition.

Turning now to FIG. 2, it can be seen that the anchor 110 can have a different number of windings 111 in different embodiments. For example, in FIG. 1, the coil 12 is a coarse pitch coil which has between two and three full windings 11, whereas in FIG. 2, the number of windings 111 is between 6 and 7. The number of windings may be keyed to the length of the strut of the device to which it will be attached, with a longer coil being employed where there is a longer space to do so. In some cases, the number of coil windings may be between 1.5 and 12 windings. In some embodiments it will be preferred to have between 2 and 4 windings, or between 2 and 3 windings. It should be noted that in the embodiment of FIGS. 2-5, elements 113, 114, 115, 117, 118, 121, 122 and 123 correspond to elements 13, 14, 15, 17, 18, 21, 22 and 23, respectively, of the embodiment described in FIG. 1.

The views of FIG. 2 show the anchor 110 with the coil 112 in one instance in a longitudinally expanded (or relaxed) state 120, and in a longitudinally compressed configuration 130. The coil 112 has spring-like properties and favors the expanded state 120 when at rest. Compression of the coil 112 in the longitudinal or axial dimension, such as by the application of a force 132, causes the inner diameter of the coil 112 to increase.

Figure 3:
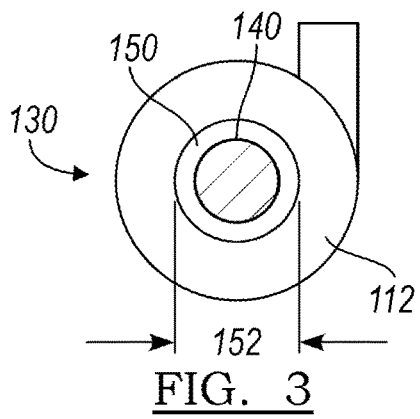
FIG. 3 is a view of the lumen of the coil of the device of FIG. 2 in the compressed condition.
Figure 4:
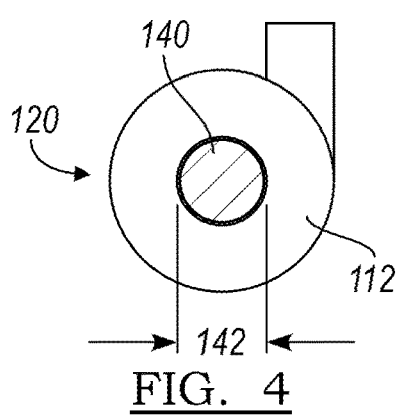
FIG. 4 is a view of the lumen of the coil of the device of FIG. 2 in the expanded condition.

FIGS. 3 and 4 illustrate the consequences of compression on the inner diameter of the coil 112. FIG. 4 shows the coil 112 in its at-rest, longitudinally-expanded configuration 120. The coil 112 defines a luminal space 140 having a first diameter 142 when at rest. When the coil 112 is compressed, the inner diameter increases, as is seen in FIG. 3, as do the dimensions of the luminal space 150. In FIG. 3, the size of the luminal space 140 is shown for reference within longitudinally compressed luminal space 150. The second inner diameter 152 in this instance is larger than the first inner diameter 142.

The spring-like behavior of the coil 112 and change in diameter allows for the coil 112 of the anchor 110 to be sized to fit about a wire portion of a medical device. The anchor 110 is maintained on the strut by a friction fit or an interference fit. That is, no adhesive, welding, soldering, crimping, or any other attachment mechanism is required to maintain the position of the anchor 110 on the medical device. It can be said that the anchor lacks such a connection to the body of the medical device by any of these means. Such a mechanism of attachment may provide a mechanical advantage, as connection methods such as soldering can change stress properties, and welding can be a technical challenge with shape memory metal components. Notably, the use of a friction fit allows for both anchor and strut to be made of a shape memory metal. Joining two pieces of shape memory material, particularly nickel-titanium alloys, can be achieved by soldering, but doing so changes the mechanical characteristics of the metal components, and soldering can expose workers to toxic chemical byproducts. The simpler workflow of creating a friction fit avoids these potential hazards. Moreover, the use of a friction fit in this way permits the joining of an anchor made from a segment of nickel-titanium (or another metal) wire to a strut which is also made of nickel-titanium wire. When wire is employed rather than cannula cutting, the cost of manufacture decreases.

Figure 5:
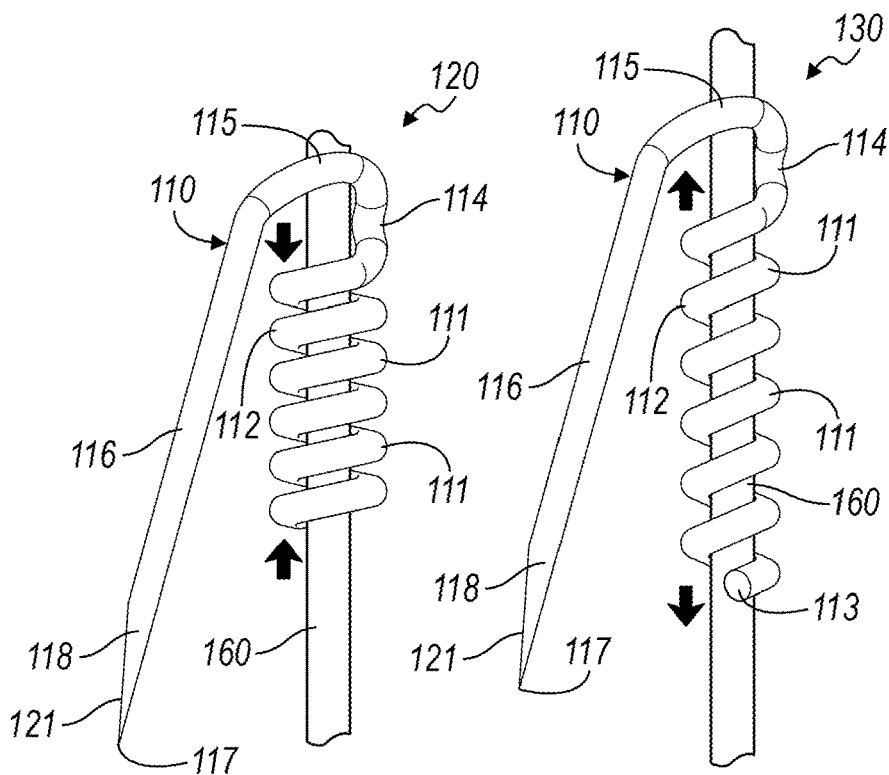
FIG. 5 is a view of the device of FIG. 2 disposed about an elongate member of a medical device (such as a strut) in a compressed and in an expanded condition.

FIG. 5 illustrates the anchor 110 in its longitudinally compressed state 130 and its longitudinally expanded state 120 when placed about a strut 160 of a medical device to achieve the aforementioned friction fit. The coil 112 of the anchor 110 has an inner diameter which is smaller than the diameter of the strut 160 of the medical device. For instance, if the diameter of the strut 160 is about 0.020 inch, the nominal diameter of the coil 112 might be about 0.016 inch. The nominal diameter of the coil may be about 50% to about 99% the diameter of the strut, or about 60% to about 95% the diameter of the strut, or about 70% to about 90% of the diameter of the strut, or about 75% to about 85% the diameter of the strut, or about 77.5% to about 82.5% the diameter of the strut, or about 80% the diameter of the strut, in order to achieve a good fit.

Figure 10A:
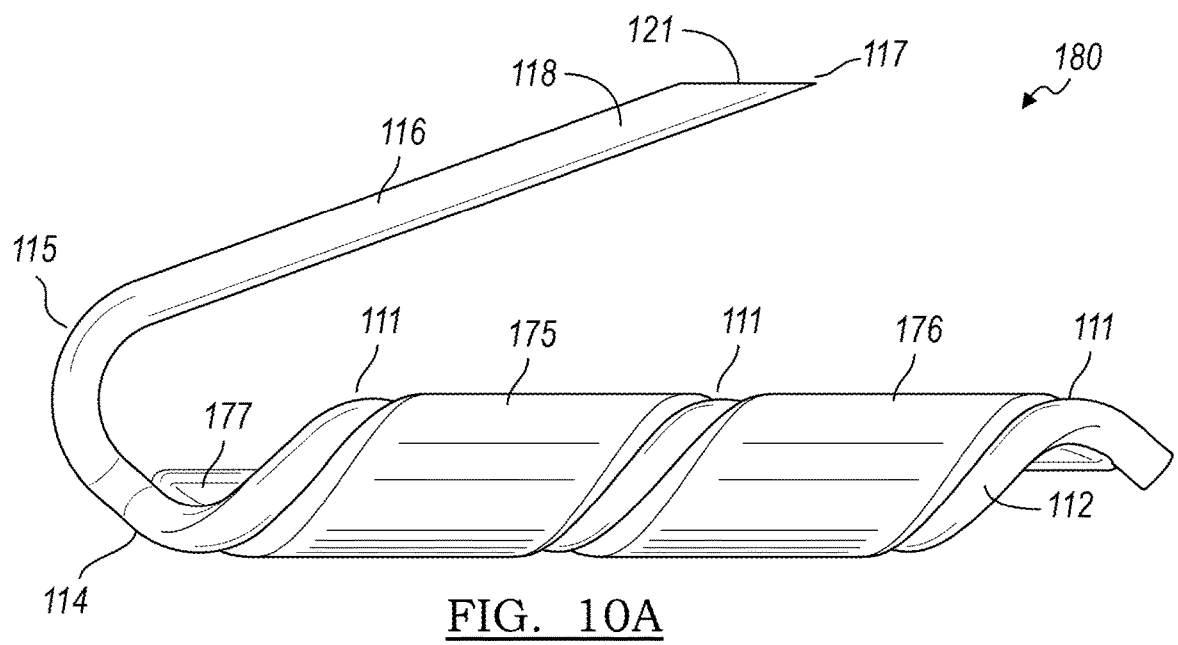
FIG. 10A is a side view of an anchor assembly including a spacer in accordance with an aspect of the present disclosure.
Figure 10B:
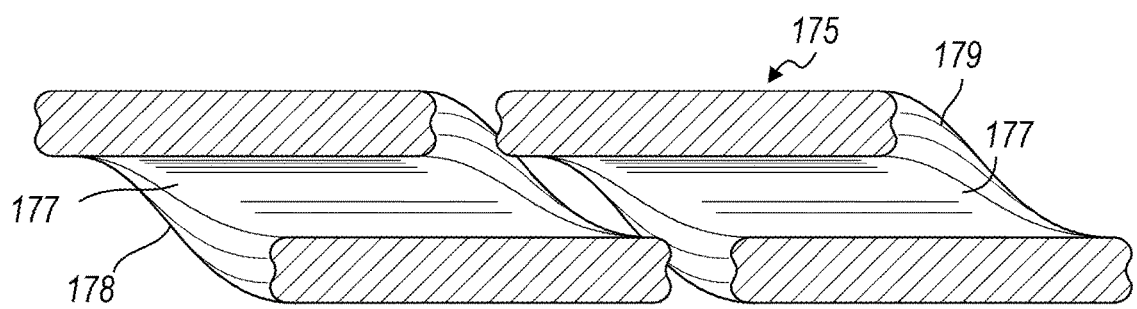
FIG. 10B is a cutaway view of the spacer of FIG. 10A.
Figure 10C:
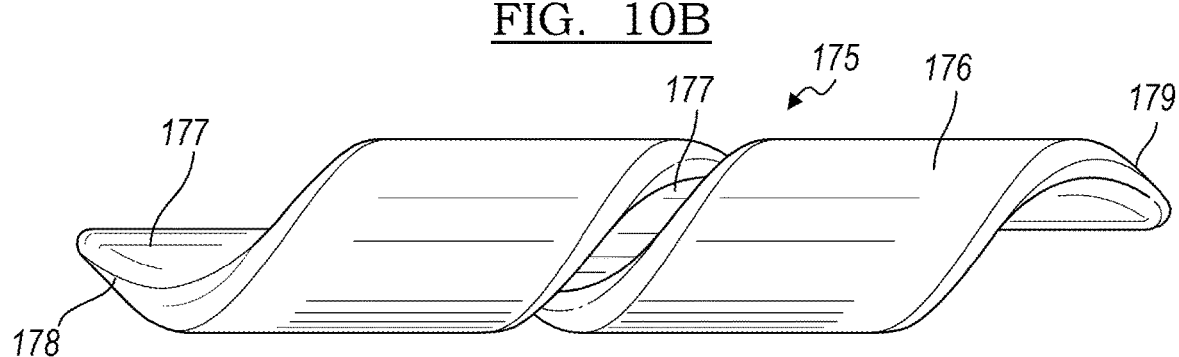
FIG. 10C is a side view of the spacer of FIG. 10A.

FIGS. 10A illustrates a portion of an anchor assembly 180 which includes an anchor 110 as described previously, as well as a spacer 175 fit between windings 111 of the coil 112. The spacer 175 may be a polymer or metal component that fits, at least in part, between windings in the longitudinal dimension, and assists in retaining the shape and configuration of the coil 112, inhibiting external forces from compressing the coil 112, causing the anchor 110 to lose its grip on the strut to which it is attached. The spacer 175 extends from a first end 178 to a second end 179, and has an outer surface 176 and an inner surface 177 opposite the outer surface 176. The inner surface 177 may contact the strut of the medical device. In some circumstances, it may be desirable to employ a single spacer 175; in other aspects, a plurality of spacers 177 may be employed. Either of the first end 178 and the second end 179 may extend beyond the ends of the coil 112, or, as shown in FIG. 10A, the first end 178 and the second end 179 may contact the coil 112. The spacer 175 has a general spiral shape.

Figure 6:
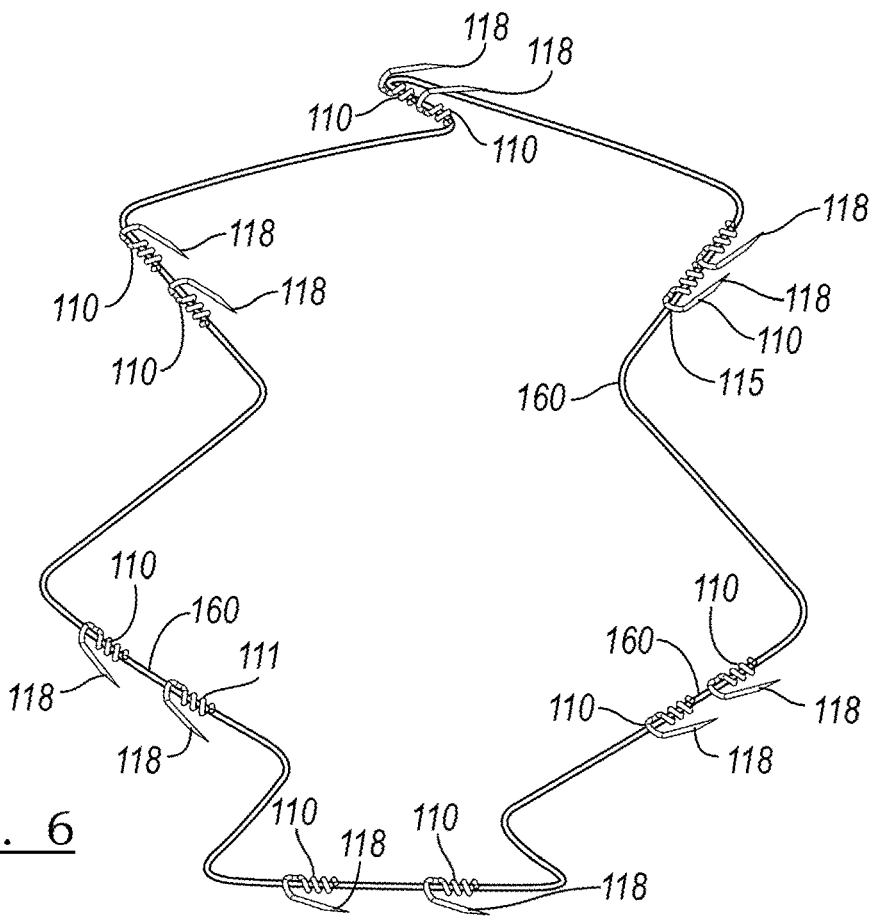
FIG. 6 is a view of a plurality of anchors formed in accordance with an embodiment of the present disclosure disposed on an end ring for a stent graft.

The anchor 110 may be affixed to the strut 160 by axial compression of the coil and releasing compression over a section of the strut 160. Axial compression results in an increase in the inner diameter to the point where the strut 160 can be inserted. When compression is released, the coil spring exerts an inward radial force when elongating proportional to the change in coil pitch (that is, the more the coil 112 elongates after compression is released, the more inward force is exerted), thereby affixing the anchor 110 to the strut 160. The barb 116 then protrudes tangent to the strut 160. FIG. 6 illustrates multiple anchors 110 attached to a wire in this way. Such a configuration could be employed in, for instance, an end ring of a stent graft.

Figure 7:
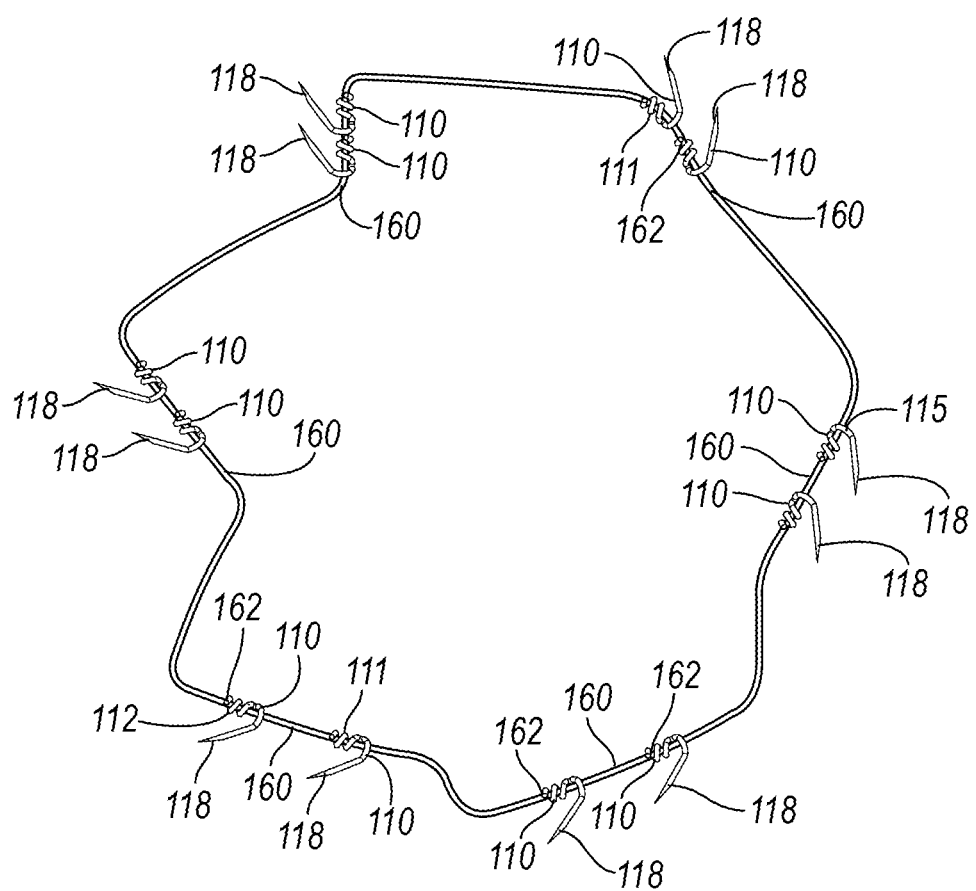
FIG. 7 is a view of a plurality of anchors welded to a stent ring by a tack weld.

FIG. 7 illustrates another way of fixing an anchor 110 to a strut 160. In this case, the coil 112 is welded to the strut 160, such as by a weld 162, which may be a tack weld at or near the extreme end of the coil 112 (that is, the end of the coil 112 that is furthest from the turn and the bend.) Such a weld may reduce the chances that a barb be twisted during deployment. In one embodiment, the weld 162 joins the very end of the coil 112 to the strut 160. In another embodiment, the weld 162 may not join the end of the coil 112 to the strut 160, but rather a portion of the coil 112 proximate the end. The weld 162 may fix less than 10%, or less than 5%, or less than 2%, or less than 1% of the length of the coil 112 to the strut 160. The weld 162 is formed such that the coil 112 is still able to stretch or contract in response to forces applied thereto during delivery and/or when deployed.

Figure 8:
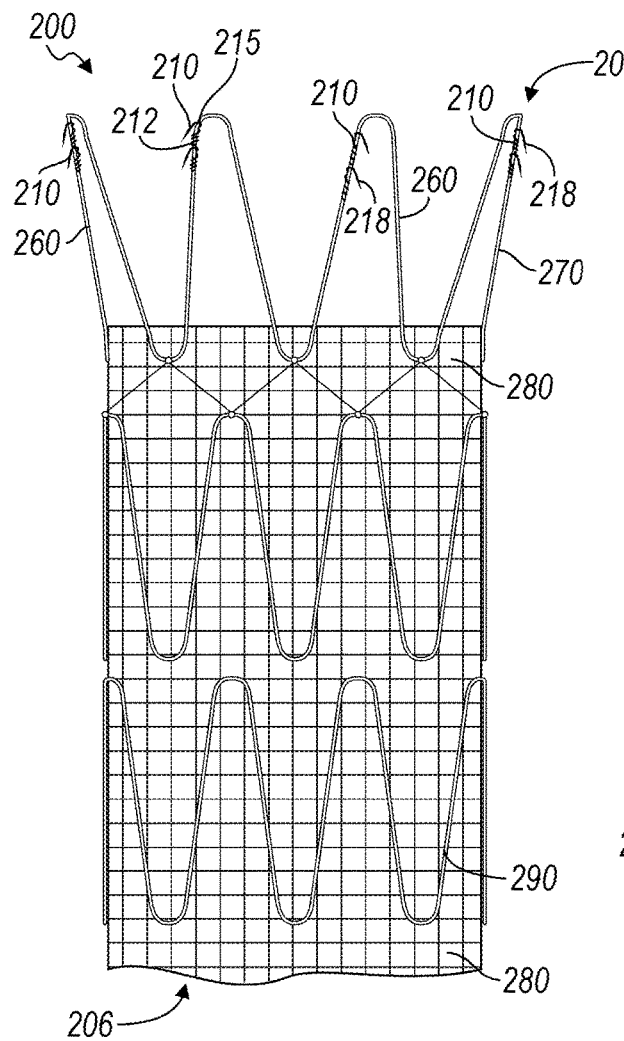
FIG. 8 is an environmental view of a plurality of anchors disposed about an end ring of a stent graft in accordance with an embodiment of the present disclosure.

FIG. 8 is an environmental view of a plurality of anchors 210 fixed to a stent graft 200. The anchors 210 are disposed at a proximal end 202 of the stent graft 200, but the barb 218 of each anchor points toward the distal end 206. The bend 215 of the anchor 210 represents the proximal-most portion of the anchor 210 when disposed on the end ring. The anchors 210 are fixed with the coils 212 disposed about the struts 260 of the end ring 270 of the stent graft 200. Distal the end ring 270 are further stent rings 290 supporting graft material 280.

Figure 9:
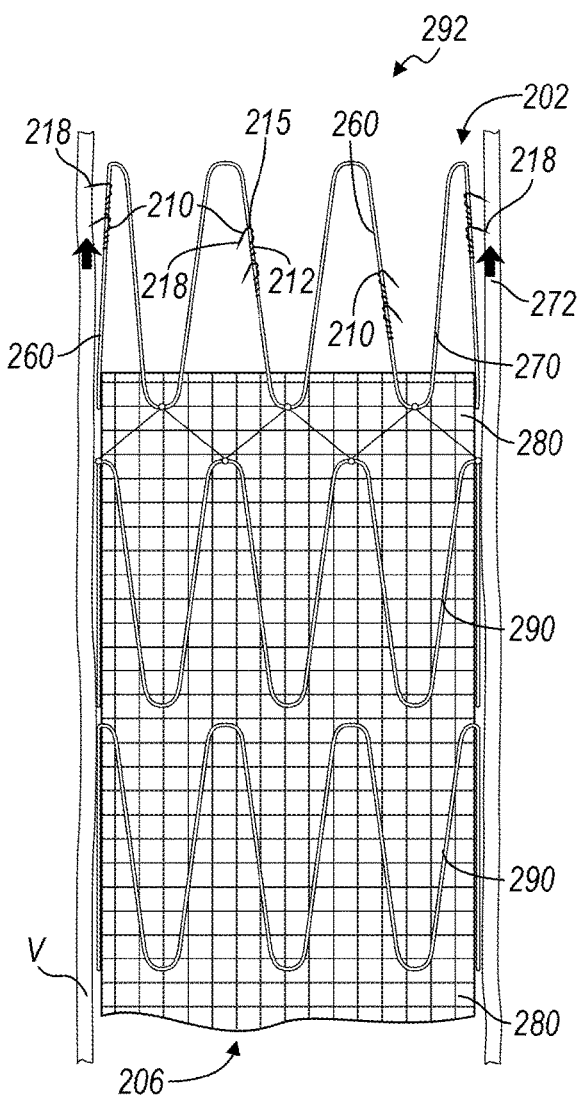
FIG. 9 is a view of the stent graft shown in FIG. 8 disposed in a body vessel.

FIG. 9 depicts the stent graft 200 deployed to a lumen 292 of a body vessel V. The barbs 218 of the anchors 210 penetrate the vessel wall, still primarily pointing distally while attached to the proximal end 202 of the stent graft 200. The hemodynamic forces 272 on the stent graft 200 that resist the fixation force of the barbs 218 will result in a moment about the barb which acts to further constrict the coil 212 about the strut 260 of end ring 270. The combined force of the shape set coil and twisting load due to fixation will provide the requisite resistance to migration, maintaining the stent graft 200 in the location to which it was originally deployed.

Although the embodiments illustrated depict stent grafts, the anchors of the present disclosure could be employed in a variety of medical devices that might be advantageously constructed of shape memory material, particularly shape memory wires. These include, but are not limited to, bare metal stents, occlusion devices, and intravascular filters.

Likewise, although the anchors of the present disclosure have only been depicted as being fixed to the end ring of a stent graft, anchors of the presently-disclosed design might be affixed anywhere along the length of a strut or a device.

As a person skilled in the art will readily appreciate, the above description is only meant as an illustration of implementation of the principles this application. This description is not intended to limit the scope of this application in that the system is susceptible to modification, variation and change, without departing from the spirit of this application, as defined in the following claims.

What is claimed is:

1. A medical device for implantation into a body passage, the medical device comprising:
    at least one elongate member; and
    an anchor attached to the elongate member, the anchor having a first end and extending to a second end, wherein the first end is a constrained end and the second end is a free end, and comprising:
    a coil defining a longitudinal axis therethrough, at least a portion of the coil surrounding the elongate member;
    a barb including the second end; and a turn of at least 90 degrees and a bend, the turn and the bend connecting the coil to the barb, such that the barb and the longitudinal axis of the coil define an acute angle therebetween, wherein when the coil is stretched longitudinally, it grips the elongate member more tightly, and wherein the anchor has a first portion extending in a first direction along the longitudinal axis that includes the coil and the turn, wherein the first direction begins at the first, constrained end and moves towards the bend, and a second portion extending in an opposing, second direction along the longitudinal axis that includes the barb, wherein the second direction begins at the bend and moves towards the second, free end, and wherein the turn is in-between the coil and the bend.

2. The medical device of claim 1, wherein the second end defines a point, such that the barb is a barb.

3. The medical device of claim 1, wherein the medical device comprises a stent.

4. The medical device of claim 1, wherein the anchor is fixed to the elongate member by a friction fit.

5. The medical device of claim 1, wherein the anchor is disposed at a proximal end of the medical device, and the second end is directed toward a distal end of the medical device.

6. The medical device of claim 1, wherein the anchor lacks a fixed connection to the elongate member by any of a weld, a solder joint, and an adhesive.

7. The medical device of claim 1, wherein the coil is compressed longitudinally to fit the anchor to the elongate member.

8. The medical device of claim 7, wherein the coil lacks a crimp about the elongate member.

9. The medical device of claim 1, where the coil has a first handedness, and the turn has a second handedness opposite the first handedness.

10. The medical device of claim 1, wherein in the coil has an inner diameter in a free condition from about 50% to about 99% the diameter of the elongate member.

11. The medical device of claim 1, wherein the coil is fixed to the elongate member by a weld.

12. The medical device of claim 1, wherein the coil comprises a plurality of windings, the medical device further comprising a spacer disposed between at least two windings in a longitudinal dimension.

13. An anchor for a medical device, the anchor having a first end and extending to a second end and comprising:
a coil defining a longitudinal axis therethrough, at least a portion of the coil configured to surround an elongate member;
a barb including the second end; and
a turn of at least 90 degrees and a bend, the turn and the bend connecting the coil to the barb, such that the barb and the longitudinal axis of the coil define an acute angle therebetween,
wherein when the coil is stretched longitudinally, it grips the elongate member more tightly,
wherein the turn curves along one side of the longitudinal axis when viewed in a first plane, and the bend curves around the longitudinal axis when viewed in the first plane,
wherein the coil and the bend are distinct structures, and
wherein when the first end is deemed a downstream end, then the coil is disposed downstream relative to the turn, and the turn is disposed downstream relative to the bend, and
wherein the acute angle is due to the first and second ends both being downstream, compared to the location of the bend.

14. The anchor of claim 13, wherein the second end defines a point.

15. The anchor of claim 14, wherein the point is defined by a cut made about 5 degrees to about 15 degrees relative to a longitudinal axis of the barb.

16. The anchor of claim 13, wherein the anchor comprises a shape memory material.

17. The anchor of claim 14, wherein the coil is movable between an expanded diameter and a compressed diameter, and is heat set to define a remembered condition at the compressed diameter.

18. The anchor of claim 13, wherein the coil has a first handedness, and the turn has a second handedness opposite the first handedness.

19. The anchor of claim 13, wherein in an expanded configuration, the coil has a length at least double a pitch of the coil.

20. An anchor for a medical device, the anchor having a first end and extending to a second end and comprising:
a coil defining a longitudinal axis therethrough, at least a portion of the coil configured to surround an elongate member;
a barb including the second end; and
a turn of at least 90 degrees and a bend, the turn and the bend connecting the coil to the barb, such that the barb and the longitudinal axis of the coil define an acute angle therebetween,
wherein when the coil is stretched longitudinally, it grips the elongate member more tightly,
wherein the turn curves along one side of the longitudinal axis when viewed in a first plane, and the bend curves around the longitudinal axis when viewed in the first plane,
wherein the coil and the bend are distinct structures, and
wherein when the first end is deemed a downstream end, then the coil is disposed downstream relative to the turn, and the turn is disposed downstream relative to the bend, and
wherein the coil has a first handedness, and the turn has a second handedness opposite the first handedness.

* * * * *